(12) United States Patent
Naumann

(10) Patent No.: US 8,562,553 B2
(45) Date of Patent: Oct. 22, 2013

(54) COMPRESSION BANDAGE

(76) Inventor: Dorethea Naumann, Veitshöchheim (DE)

(*) Notice: Subject to any disclaimer, the term of this patent is extended or adjusted under 35 U.S.C. 154(b) by 919 days.

(21) Appl. No.: 12/088,355

(22) PCT Filed: Sep. 6, 2006

(86) PCT No.: PCT/DE2006/001562
§ 371 (c)(1),
(2), (4) Date: Jul. 29, 2008

(87) PCT Pub. No.: WO2007/036191
PCT Pub. Date: Apr. 5, 2007

(65) Prior Publication Data
US 2009/0143709 A1 Jun. 4, 2009

(30) Foreign Application Priority Data
Sep. 29, 2005 (DE) .......................... 10 2005 047 584

(51) Int. Cl.
*A61L 15/00* (2006.01)
(52) U.S. Cl.
USPC .................. 602/75; 602/76; 450/75; 450/93; 139/422
(58) Field of Classification Search
USPC .......... 602/41, 75–76, 60–65; 428/92, 95, 97, 428/99; 139/383 R, 407, 420 A, 420 R, 421, 139/422, 426 R; 450/36, 39, 58, 70, 75, 79, 450/81, 85, 93
See application file for complete search history.

(56) References Cited

U.S. PATENT DOCUMENTS

| | | | | |
|---|---|---|---|---|
| 3,561,442 A | * | 2/1971 | Goswitz | 602/41 |
| 3,660,215 A | * | 5/1972 | Pawlicki | 428/593 |
| 3,970,079 A | * | 7/1976 | Gaylord, Jr. | 602/19 |
| 4,207,885 A | * | 6/1980 | Hampton et al. | 602/76 |
| 7,135,007 B2 | * | 11/2006 | Scott et al. | 602/75 |

* cited by examiner

*Primary Examiner* — Patricia Bianco
*Assistant Examiner* — Camtu Nguyen
(74) *Attorney, Agent, or Firm* — Edwin D. Schindler

(57) ABSTRACT

A compression bandage shaped as an elongate rectangle is made of a textile fabric on which a hook strip is fastened along a narrow side of a small portion of a lateral face, or hook side. The fabric contains elastic filaments running in a longitudinal direction and, in a transverse direction, includes virtually inelastic supporting filaments having a spring constant in the longitudinal direction that ranges from 0.3 to 3 Newtons/cm of longitudinal stretching and a per meter length and per decimeter width of the compression bandage. Small loops made of soft filaments are interwoven and distributed uniformly over the entire area of the lateral face, or fleece side, opposite the hook strip. These small loops are oriented approximately perpendicularly to the lateral face, in size and distance from one another, and are complementary to the hooks of the hook strip for forming a releasable hook-and-loop closure.

4 Claims, 3 Drawing Sheets

COMPRESSION BANDAGE

BACKGROUND OF THE INVENTION

1. Technical Field of the Invention

The invention relates to a compression bandage in the form of an elongated rectangle made of a textile fabric, on which a hook strip is fastened along a narrow side on a small portion of a lateral face, the hook side, the fabric containing elastic filaments running in a longitudinal direction and, in the transversal direction, consists of virtually inelastic supporting filaments.

2. Description of the Prior Art

In the case of operations in the region of the breast, e.g. shape changes of the breasts or, in the case of heart operations, large internal wound areas remain, which are pressed together by means of an external compression bandage until they have developed sufficient inherent stability as a result of the healing. Otherwise, cavities occur, which result in a delay of the healing process and increased scarring.

Scars are unwelcome, particularly in the case of plastic surgery on the breast. Therefore, in the prior art, a bandage is placed around the patient's breast after the operation. This bandage is elastic and exerts an adjustable pressure on the entire covered region of the thorax and therefore also on the scar. As a result, the wound areas and the edges of the wound are pressed together and the process of healing is supported, accelerated and the results improved.

In the prior art, elastic bandages are, inter alia, used for this. However they can only be applied after the operation with some difficulty, since they usually must be placed several times around the thorax. Because of their soft characteristics, this requires lifting the patient or sitting the patient up, which can harm the wound. Although conventional hook-shaped closures can be applied to any point on the elastic bandage, the hook represents a risk of injury for the skin region lying below it. Elastic bandages have the tendency to slip, to constrict and not to maintain constant compression over a sufficiently long period.

A common alternative is elastic bands with a short hook-and-loop closure. This hook-and-loop closure consists of a hook strip at one end of the elastic strip and the fleece strip at the other end of the strip, on the other side. A disadvantage of this principle is that the hook strip and fleece strip must, to a large extent, cover one another, since the hook strip does not adhere on the other regions of the elastic strip. As a result, on application, the active length can only be varied within the small limits of the length of the hook strip and the fleece strip. Doubling of the compressive force is therefore impossible in practice There are also complaints of the tendency to constrict and form wrinkles. That is particularly problematic under the hook-and-loop fastening, since constrictions and wrinkles cause pressure points on the skin, which lead to skin injuries in the long term.

These effects greatly obstruct the healing process in the wound area and lead to a scar that is both optically and haptically unsatisfactory. Consequently, the chief aim of undisturbed healing is not provided.

In the prior art, so-called "thorax compression shirts" are used, which contain elastic filaments and thereby press on the skin. However, it is disadvantageous that the compressive pressure can hardly be varied and also that thorax shirts of different size increments must be kept in stock for patients of different sizes.

SUMMARY OF THE INVENTION

It is the object of the invention to provide a compression bandage of a rectangular section of a textile material, which only requires a hook strip at one end and does not require a separately mounted fleece strip.

This object is achieved according to the invention in that the spring constant in the longitudinal direction ranges lies in the order of magnitude of 0.3 to 3 Newtons per centimeter of longitudinal stretching and per meter length and per decimeter width of the compression bandage and small loops made of soft filaments are interwoven distributed uniformly over the entire area of the lateral face opposite the hook strip, the fleece side, these small loops being oriented approximately perpendicular to the lateral face and, in size and distance from one another, are complementary to the hooks of the hook strip, and with them, together with the hook strip, a releasable hook-and-loop closure can be formed.

A significant characterizing feature of the invention is, thus, that the elasticity of the compression bandage lies in order of magnitude within the range of about 0.5 to 3 Newton per centimeter of longitudinal extension and per meter length and per decimeter width. That means that a 1-meter-long and 10-centimeter-wide section of a compression bandage according to the invention, which is firmly clamped at one end over its entire length and is stretched at the other end by one centimeter length by means of a clamping device, which also extends over the entire width, requires a force between about ⅓ and 3 Newtons for this.

If the material section is of double the length, that is to say 2 meters, then only half the force is required for the lengthening by one centimeter, that is to say ¼ to 1.5 Nm.

If a material section of one meter length has double the width, that is to say 2 dm, equal to 20 cm, then twice the force is required for the lengthening by one centimeter, that is to say 1 to 6 Nm.

Such a compression bandage offers numerous advantages. The hook band can be placed and pressed on at any arbitrary point on the bandage, by this means the number of different sizes to be kept in stock is noticeably reduced.

It also offers numerous advantages from a medical point of view after the operation, for example, the bandage, thanks to its stiffness, can be pushed in a longitudinal direction under the patient's back, and, in this way, applied while the patient is still reclining, that is to say without further mechanical stressing of the operation scars.

Because of the hook-and-loop closure, which can be applied at any desired point, a very high compressive pressure can be adjusted after the operation has ended. The danger of bleeding and swelling are, in medical experience, particularly small if the compressive pressure is set to twice the value that is appropriate after two to three days. In addition, the pressure should be reduced to an intermediate value after a few hours.

DETAILED DESCRIPTION OF THE PREFERRED EMBODIMENTS

An advantage of the compression bandage according to the invention is that only two manual operations are needed for these adjustments and that, as a result of the transverse stiffness of the compression bandage, the risk of forming wrinkles and constrictions is noticeably reduced. A further advantage is that the compressive pressure is distributed much more uniformly over the entire width of the bandage than in the case of the variants known hitherto. These advantages are particularly important because the patient regularly has to take off the compression bandage for personal hygiene. When it is reapplied, it is important that the doctor adjusts the compressive pressure as accurately as possible. That can be done by means of a simple mark. It is also advantage that the risk of wrinkling and constriction is also considerably reduced.

A compression bandage according to the invention can be manufactured in some interesting variants. This includes weaving at least one elastic filament in the edge regions with much higher elasticity value than in the center region. By this means, the transition from the compressed skin region below the compression bandage to the unbandaged region is distributed over a larger strip, and the risk of forming impression marks of the bandage edge and/or resulting stresses or even injuries is greatly reduced.

A further variant provides weaving resilient rods in the transverse direction of the bandage. These rods help to smooth the bandage when it is applied. They thereby permit more rapid application without the risk of forming wrinkles. In a preferred embodiment of the invention, these resilient rods have a cross-section at their center region that is larger than their cross-section at their end regions.

A further variant of a compression bandage according to the invention, which is interesting for application in the case of breasts, is the integration of hollow spherical segments. To this end, the invention proposes that a hollow spherical segment is fixed on the outside, which is connected not only at the edge, but also to the fabric at points distributed uniformly over the inside surface. The dimensions of this hollow spherical segment must be matched to the size of the breast to be supported. Two almost identical parts are required; the patient thus has two hook-and-loop connections. With the first connection between the breasts, the bandage is adjusted to the distance between the breasts; with the second connection the two bandage parts are applied to the extent that they do not show any gaps between the body and bandage. Below, the compression is adjusted to the necessary value by stepwise shortening of the bandage alternately between the front and rear closures. The continuous changing between the two closures helps to maintain the orientation of the two hollow spherical segments to the two breasts. Such an arrangement can replace the thorax shirt, which was conventionally used if it is vertically fixed by means of the support strips described below. The advantage of this arrangement is that, in contrast to a thorax shirt, it can be repeatedly adjusted and thereby adapted to the patient.

Another variant of a compression bandage according to the invention, which facilitates its use, describes a stabilization strip, which is fixed at as many points as possible distributed uniformly in the longitudinal direction, or integrated into the fabric. In this case, the stabilization strip is oriented approximately perpendicularly to the elastic filaments and extend over the greatest possible portion of the width of the bandage. Materials suitable for the stabilization strip are resilient plastics and/or rustproof metals. The advantage of this device is that, even with less careful pressing of the hook strip by the stabilization strip, it is ensured that the corners, for example, do not bulge upwards and thereby only a part of the surface of the hook strip is seated on the fleece side of the bandage and, in this manner, generates a compression that is non-uniformly distributed in the transverse direction.

A further user-friendly complement of the compression bandages according to the invention comprises bearing strips, which consist of textile material that is virtually inelastic in the longitudinal direction, and which are joined, by means of one hook strip in each case, at their two narrow sides, to two arbitrary points on the fleece side of the bandage. The fastening of these bearing strips by means of hook-and-loop fastenings is permitted by a very rapid and accurate fastening and removal. In particular, with very slim or extremely overweight patients, the problem of slipping of the compression bandage vertically is solved in that the bearing strips are guided forward over shoulders, in a similar way to trouser support braces, on the back side of the compression bandage, and are again attached on the breast by means of the hook-and-loop fastenings.

It is of advantage if the support strips have a lengthwise adjustment because the stocking of different types is thereby avoided and because thereby the hook-and-loop fastening on the region of the compression bandage is restricted and not pressed on the skin regions lying adjacently.

Suitable mechanisms for lengthwise adjustment are the return buckles conventional for rucksacks and helmets. Another alternative is, for example, to divide the support strip into two halves. At the end of one half, a rectangular metal ring if fixed by means of a loop; the other part of the support strip is guided through this ring. In a logically consistent manner, an adjustment of the length is provided by means of a hook-and-loop fastening close to the square ring should also be provided on this second half of the support strip.

To permit an as far as possible infinitely variable adjustment, it is advisable here to produce the support strip from a similar material to the compression bandage, but instead of the elastic filament to use filaments in the longitudinal direction that are as inelastic and highly load-bearing as possible, but so flexible at the sides that they can be formed around the metal ring into a very small loop.

Another variant of this support strip is that it only has a hook strip at one end that is mounted directly on the compression bandage. At the other end, a fastening means, such as a resilient clip, a button, a press stud, a pin or a hook is fixed, with which the support strip can be fixed on articles of clothing of the patient. A possible application is for adipose patients, with which the compression bandage can be easily displaced towards the head. A downwardly directed support strip, which is fixed on suitable soft trousers, is used to secure the compression bandage at the bottom.

A principal advantage of the compression bandages according to the invention is the gradual adjustment of the compressive pressure. As mentioned above, a compressive pressure of up to 55 mm Hg is adjusted in the first two or three hours after the operation. It is most advantageous if, to this end, the compression bandage is stretched to the extent that it overlaps itself in the region of the scar by values of the order of magnitude of about a half meter. By means of the overlapping, a further stability of the bandage is achieved transverse to its longitudinal axis, which counteracts disadvantageous rubbing movements in the region of the wound.

After about two to three hours, the compression bandage should be loosened until the compression values, depending on the individual case, lie in a region between around 35 and 45 mm Hg. Then the bandage is adjusted to a value between around 25 and 35 mm Hg. An advantage of the compression bandage is that these compression values are associated with a very specific contact point on the fleece side, which the treating doctor can mark on the copy used by the patient, whereby it is ensured that, after cleaning of the compression bandage and/or of the patient on reapplication, the necessary compressive pressure can be readjusted with high accuracy.

BRIEF DESCRIPTION OF THE DRAWING FIGURES

Further details and features of the invention are explained below in greater detail with reference to examples. The illustrated examples are not intended to restrict the invention, but only to explain it. In schematic view.

DETAILED DESCRIPTION OF THE DRAWING FIGURES AND PREFERRED EMBODIMENTS

Figure 1:
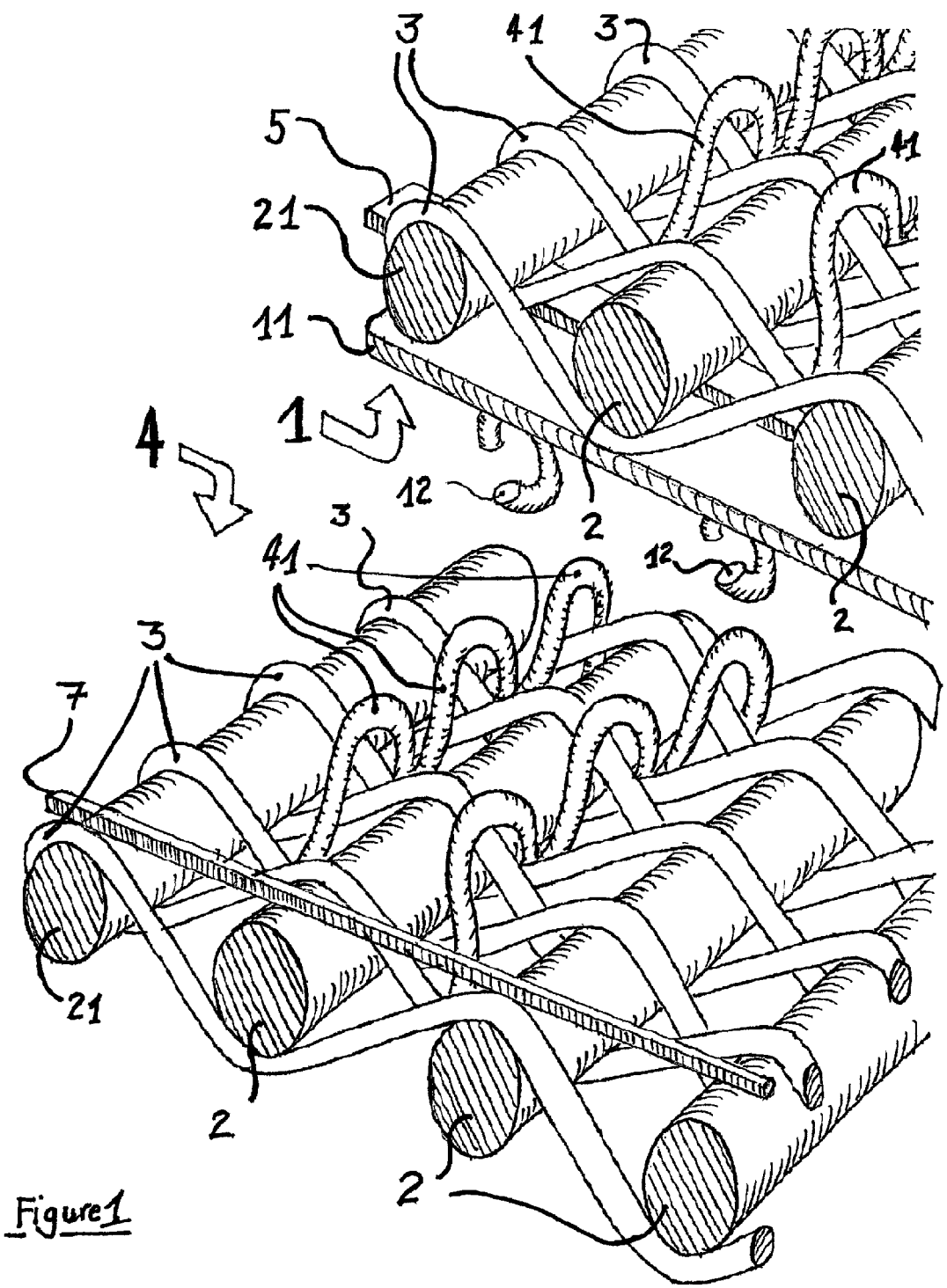
FIG. 1 shows a detail of the fabric with loops and hooks.

In detail, the figures show:

FIG. 1 shows a cross-section through a detail of the fabric of a compression bandage according to the invention. The cross-cut elastic filaments 2 can be seen, which run linearly in the longitudinal direction of the bandage. In the transverse direction, the supporting filaments 3 are looped around the elastic filaments 2. The loops 4 are interwoven into the fabric comprising support filaments 3 and elastic filaments 2. In the upper half of FIG. 1, the other end of the compression bandage can be seen. Also on the fleece side 4, some loops 41 are illustrated, though, for the sake of clarity, not in their full number at all crossing points of the fabric.

Opposite the fleece side 4 of the compression bandage is the hook side 1. FIG. 1 shows why it bears this name: The hook strip 11 is fixed on this side at one end. The hook strip 11 as known in the prior art consists of a backing fabric, which runs parallel to the fabric of the compression bandage, transversely thereto the hooks 12 are interwoven into the hook strip 11. In FIG. 1, it is clear that the individual hooks 12 are complementary in shape and size to the loops of the compression bandage. In the illustrated position, hooks 12 and loops 41 are already led so close to one another that they only need to make a short residual movement to interlock with one another.

The principle course of a stabilization strip 7 is drawn. However, in practical embodiments, it has a considerably larger cross section compared to the elastic filaments 2, depending on the material.

Figure 2:
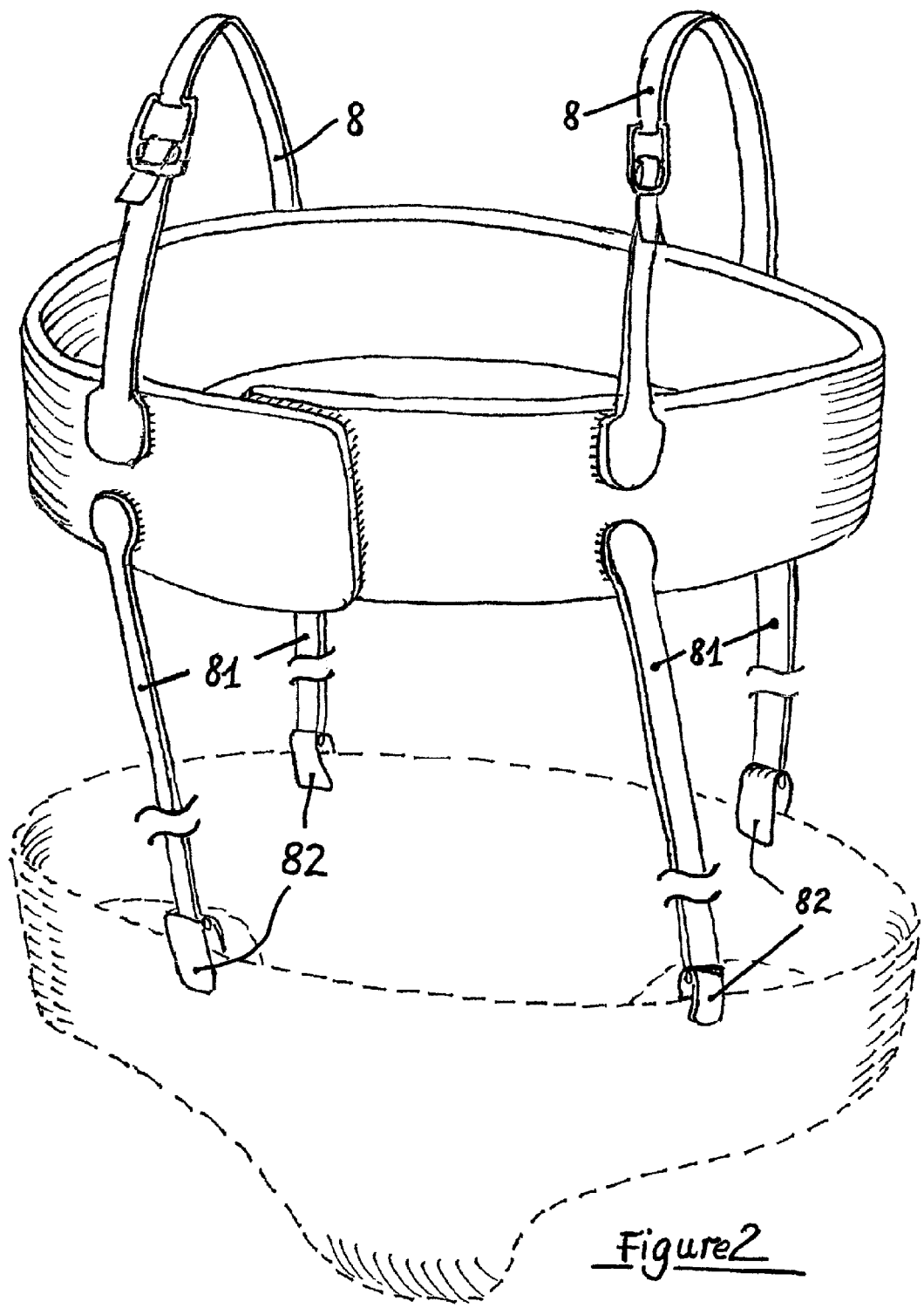
FIG. 2 shows a compression bandage equipped with support straps at the top and bottom.

FIG. 2 shows how a compression bandage according to the invention can be extended to a complete breast compression bandage system, in which support strips 8 are fixed on the fleece side 4 of the bandage by means of hook-and-loop fastenings, which secure the bandage against slipping upward and downward. FIG. 2 shows how a compression bandage can be secured upwardly by means of two support strips 8. They are fixed with hook and loop fastenings on the breast side of the bandage, from there, pass over the shoulders until the other end is fixed with hook-and-loop fastenings on the reverse region of the bandage. The option for lengthwise adjustment of the support strips is shown. At the bottom, in the illustrated example, the bandage is fixed by means of a total of four support strips 81, which are fastened on the bandage by means of hook-and-loop strips and, at the other end, can be fixed on an article of clothing of the patient, specifically underpants in the illustrated example, in the principle of a stocking suspender.

Figure 3:
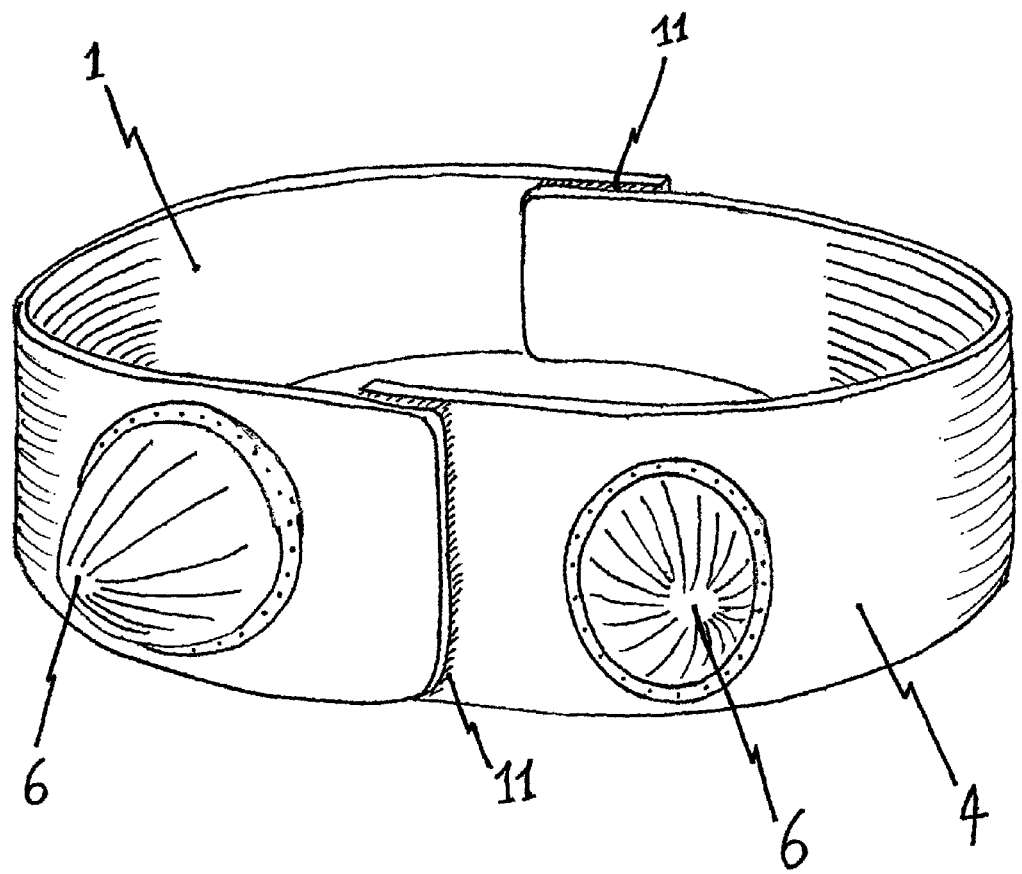
FIG. 3 shows two-part compression bandage with mounted hollow spherical elements principally for female breasts.

FIG. 3 shows a further embodiment of a compression bandage. It can be seen that, in this example, it consists of two parts, which are connected by means of a hook-and-loop fastening on the breast side and the back side. Each half of the compression bandage bears a mounted hollow spherical segment 6. From FIG. 3, it can be derived that the front hook-and-loop fastening primarily serves for adjusting the distance between the breasts to suit the patient, and the back-side hook-and-loop fastening is primarily used for adjusting the required compressive pressure. It is clear that with increasing compressive pressure, however, the short portion of the bandage between the hollow spherical segment 6 and hook-and-loop fastening becomes somewhat long, so that with the process of also adjusting the correct compressive pressure on the breast-side hook-and-loop fastening for optimum positioning of the hollow spherical segment 6, a small readjustment becomes necessary.

LIST OF REFERENCE CHARACTERS

1 Hook side
11 Hook strip
12 Hook on hook strip 11
2 Elastic filament
21 Elastic filament, as 2 but with greater elasticity
3 Support filament
4 Fleece side
41 Loop, projects out of the fleece side 4
5 Rod
6 Hollow spherical segment
7 Stabilizing strips in the transverse direction
8 Support strips
81 Support strips as 8, but with a fastening means 82 at one end
82 Fastening means

The invention claimed is:

1. A compression bandage, comprising:
a textile fabric shaped as an elongated rectangle;
a hook strip comprised of hooks and fastened along a small portion of a first lateral face of said textile fabric defining a hook side thereof;
elastic filaments running linearly in a longitudinal direction along said textile fabric and having, in a transverse direction, virtually inelastic supporting filaments, said elastic filaments having a spring constant in the longitudinal direction of 0.3 to 3 Newtons/cm of longitudinal stretching per meter length per decimeter width; and,
a fleece side of said textile fabric having loops of soft filaments interwoven and uniformly distributed over a second lateral face positioned oppositely said hook strip, said loops being oriented approximately perpendicularly to said second lateral face and, in size and distance from one another, being complementary to said hooks of said hook strip, said fleece side and said hook side forming a releasable hook-and-loop closure.

2. The compression bandage according to claim 1, further comprising resilient rods attached to said fleece side of said textile fabric.

3. The compression bandage according to claim 1, further comprising a hollow spherical segment fixed on said fleece side, said textile fabric being fixed at an edge of said hollow spherical segment and at points uniformly distributed over an inner surface of said hollow spherical segment.

4. The compression bandage according to claim 1, wherein said supporting strip includes means for adjusting a length of said supporting strip.

* * * * *